United States Patent [19]

Le et al.

[11] Patent Number: 6,025,386
[45] Date of Patent: Feb. 15, 2000

[54] SYNERGISTIC INSECTICIDAL COMPOSITIONS

[75] Inventors: Dat Phat Le, North Wales, Pa.; Guy Julius Smagghe, Temse, Belgium

[73] Assignee: Rohm and Haas Company, Philadelphia, Pa.

[21] Appl. No.: 09/391,827

[22] Filed: Sep. 8, 1999

Related U.S. Application Data

[62] Division of application No. 09/233,772, Jan. 19, 1999
[60] Provisional application No. 60/073,473, Feb. 3, 1998.

[51] Int. Cl.[7] .......................... A01N 43/08; A01N 43/16; A01N 43/30; A01N 43/32
[52] U.S. Cl. .......................... 514/452; 514/456; 514/466; 514/469; 514/547
[58] Field of Search ...................................... 514/452, 456, 514/466, 469, 547

[56] References Cited

U.S. PATENT DOCUMENTS

| | | | |
|---|---|---|---|
| 5,378,726 | 1/1995 | Yanagi et al. | 514/456 |
| 5,530,028 | 6/1996 | Lidert et al. | 514/649 |

OTHER PUBLICATIONS

Martin et al, "Effects of Selected Synergists on Insecticide toxicity in tobacco Budworm" J. Econ. Entomol, (1997) 90(3), 723–731.

*Primary Examiner*—Allen J. Robinson
*Attorney, Agent, or Firm*—Thomas D. Rogerson

[57] ABSTRACT

This invention relates to insecticidal compositions comprising one or more substituted N,N'-dibenzoyl-N'-tert-alkyl-hydrazines and diethyl maleate which exhibit improved activity as insecticides when compared to compositions without diethylmaleate.

7 Claims, No Drawings

SYNERGISTIC INSECTICIDAL COMPOSITIONS

This application is a divisional application of application Ser. No. 09/233,772, filed Jan. 19, 1999, which claims the benefit of U.S. Provisional application Ser. No. 60/073,473, filed Feb. 3, 1998.

Insecticidal compositions containing N,N'-dibenzoyl-N'-tert-alkyl-hydrazines are known. Although such compositions may be effective against some insects, there is a continuing need for compositions which are either more efficacious against a broader spectrum of insects or require lower amounts of N,N'-dibenzoyl-N'-tert-alkyl-hydrazine to provide the same level of effectiveness as a matter of conservation, environmental concern and cost.

We have discovered that compositions comprising an insecticidal N,N'-dibenzoyl-N'-tert-alkyl-hydrazine and diethyl maleate ("DEM") exhibit improved activity as insecticides when compared to compositions without DEM and, therefore, provide a sought-after improvement in effectiveness.

This invention is a composition comprising:
a) one or more N,N'-dibenzoyl-N'-tert-alkyl-hydrazines of the formula:

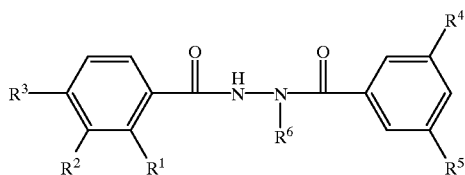

wherein:
i) $R^1$, $R^4$, and $R^5$ are independently hydrogen, $(C_1-C_4)$ alkyl, $(C_1-C_4)$alkoxy, or halo;
ii) $R^2$ and $R^3$ are:
  1) independently hydrogen, $(C_1-C_4)$alkyl, $(C_1-C_4)$ alkoxy, or halo; or
  2) joined together with the benzoyl ring carbons to which they are attached to form a 5 or 6-membered carbocyclic, dioxolano, dioxano, oxano, or oxolano ring such that when in the form of a 5-membered ring $R^2$ and $R^3$ together is —A—$CH_2$—$A^1$—and when in the form of a 6-membered ring $R^2$ and $R^3$ together is —A—$CH_2CH_2$—$A^1$—, wherein A and $A^1$ are independently —$CH_2$— or —O—; and
iii) $R^6$ is a $(C_4-C_{10})$alkyl group containing a tertiary carbon; and b) diethyl maleate.

Such compositions may further comprise one or more agronomically acceptable carriers.

The term "alkyl" by itself or as a part of another substituent, unless otherwise stated, means straight and branched chain groups such as methyl, ethyl, propyl, iso-propyl, butyl, iso-butyl, sec-butyl, and tert-butyl. The term "alkoxy" by itself or as a part of another group includes, for example, methoxy, ethoxy, propoxy, iso-butoxy, and the like. The term "halo" means fluoro, chloro, bromo, and iodo.

Preferably, $R^1$, $R^2$, $R^3$, $R^4$, and $R^5$ are independently hydrogen, methyl, ethyl, Methoxy, ethoxy, bromo, chloro, or fluoro. More preferably, $R^1$, $R^2$, and $R^3$ are independently hydrogen, methyl, ethyl, methoxy, ethoxy, or chloro. Most preferably; a) $R^1$ is methyl or ethyl, $R^2$ is methoxy, and $R^3$ is hydrogen, or b) $R^1$ and $R^2$ are hydrogen and $R^3$ is chloro or ethyl. $R^4$ and $R^5$ are preferably hydrogen, chloro, or methyl, most preferably methyl. $R^6$ is preferably a tert-$(C_4-C_6)$alkyl, more preferably tert-butyl. Preferred N,N'-dibenzoyl-N'-tert-butyl-hydrazines of this invention are N'-(benzoyl)-N-(4-chlorobenzoyl)- N'-tert-butyl-hydrazine; N-(4-ethylbenzoyl)-N'-(3,5-dimethylbenzoyl)-N'-tert-butyl-hydrazine and N'-(3,5-dimethylbenzoyl)-N-(3-methoxy-2methylbenzoyl)-N'-tert-butyl-hydrazine.

By "agronomically acceptable carrier" is meant any substance or mixture of substances which can be utilized to dissolve, disperse or diffuse the compound incorporated therein without impairing the effectiveness of the compound and which does not create permanent damage to soil, equipment, and agronomic crops when utilized according to recommendations.

The relative proportion of the amount of DEM to N,N'-dibenzoyl-N'-tert-alkyl-hydrazine compounds in the embodied composition is that proportion which results in unexpected synergistic efficacy when compared to an identical composition of the N,N'-dibenzoyl-N'-tert-alkyl-hydrazine without added DEM. For such compositions the relative proportions by weight of the amount of DEM to N,N'-dibenzoyl-N'-tert-alkyl-hydrazine compounds ranges from 0.01:1 to 100:1. Preferably, the range is from 1:1 to 10:1. More preferably, the range is from 4:1 to 6:1. Most preferably, the ratio is 5:1.

The compositions of the present invention can be applied to various loci such as soil or foliage. The compositions may contain from 0.01 to 99.9 percent combined weight of DEM and N,N'-dibenzoyl-N'-tert-alkyl-hydrazine. More typically the compositions will contain from 1.0 to 85 percent combined weight of amount of DEM and N,N'-dibenzoyl-N'-tert-alkyl-hydrazine. The compositions are usually taken up in a carrier or are further formulated so as to render them suitable for subsequent dissemination as insecticides. For example, these chemical agents can be formulated as solutions, wettable powders, emulsifiable concentrates, dusts, granular formulations, pellets, aerosols, or flowable emulsion concentrates. In such formulations, the compositions are extended with liquid or solid carriers and, when desired, suitable surfactants are incorporated.

It is usually desirable, particularly in the case of foliar spray formulations, to include one or more adjuvants, such as wetting agents, spreading agents, dispersing agents, stickers, adhesives, emulsifying agents and the like in accordance with agricultural practices. Such adjuvants commonly used in the art can be found in the John W. McCutcheon, Inc. publication "Detergents and Emulsifiers, Annual." Allured Publishing Company, Ridgewood, N.J., U.S.A.

The compositions of this invention may be prepared using a variety of methods. For example, the DEM and N,N'-dibenzoyl-N'-tert-alkyl-hydrazine can be taken up on or mixed with a finely divided solid carrier, as for example, clays, inorganic silicates, carbonates, and silicas. Organic carriers can also be employed.

The compositions may be prepared as dust concentrates which are commonly made wherein the DEM and N,N'-dibenzoyl-N'-tert-alkyl-hydrazine are present in the range of about 20% to 80%. For ultimate applications, these concentrates are normally extended with additional solid to give an active ingredient content of from 0.1 to about 20%. Granular formulations are made using a granular or pelletized form of carrier, such as granular clays, vermiculite, charcoal or corn cobs, and may contain the active ingredient from about 1 to about 25% by weight.

Wettable powder formulations are made by incorporating the DEM and N,N'-dibenzoyl-N'-tert-alkyl-hydrazine in an inert, finely divided solid carrier along with a surfactant which can be one or more emulsifying, wetting, dispersing, or spreading agents or a blend of these. The combined DEM and N,N'-dibenzoyl-N'-tert-alkyl-hydrazine are usually present in the range of about 10 to about 80% by weight and surfactants in from about 0.5 to about 10% by weight. Commonly used emulsifying and wetting agents include polyoxyethylated derivatives of alkylphenols, fatty alcohols, fatty acids, alkylamines, alkylarene sulfonates and dialkyl sulfosuccinates. Spreading agents include such material as glycerol mannitan laureate and a condensate of polygylcerol and oleic acid modified with phthalic anhydride. Dispersing agents include such materials as the sodium salt of the copolymer of maleic anhydride and an olefin such as diisobutylene, sodium lignin sulfonate and sodium formaldehyde naphthalene sulfonates.

Water dispersible granular products may be prepared by granulating or agglomerating a suitable wettable powder formulations which is compatible with the active ingredients. Agglomeration is typically carried out in a conventional manner such as by a pan agglomerator.

Emulsifiable concentrate formulations are prepared by dissolving the DEM and N,N'-dibenzoyl-N'-tert-alkyl-hydrazine in an agronomically acceptable organic solvent and adding a solvent-soluble emulsifying agent. Suitable solvents are usually water-immiscible and can be found in the hydrocarbon, chlorinated hydrocarbon, ketone, ester, alcohol and amide classes of organic solvents. Mixtures of solvents are commonly employed. The surfactants useful as emulsifying agents may constitute from 0.5 to 10% by weight of emulsifiable concentrates and may be anionic, cationic or non-ionic in character. The combined concentration of the DEM and N,N'-dibenzoyl-N'-tert-alkyl-hydrazine may vary from 10 to 80%, preferably in the range of from 25 to 50%.

The compositions can be applied as insecticidal sprays by methods commonly employed, such as conventional high-liter hydraulic sprays, low-liter sprays, air-blast spray, aerial sprays, and dusts. The dilution and rate of application will depend upon the type of equipment employed, the method of application, crop treated, and insects to be controlled, but the effective amount is usually from 0.01 Kg. to 10 Kg. of the N,N'-dibenzoyl-N'-tert-alkyl-hydrazine per hectare. Preferred amounts are from 0.1 Kg to 1 Kg of the N,N'-dibenzoyl-N'-tert-alkyl-hydrazine per hectare.

The compositions of this invention can also be mixed with fertilizers or fertilizing materials before their application. In one type of solid fertilizing composition, particles of a fertilizer or fertilizing ingredients, such as ammonium sulfate, ammonium nitrate, or ammonium phosphate, can be coated with one or more of the compositions. Solid compositions and solid fertilizing material can also be admixed in mixing or blending equipment, or they can be incorporated with fertilizers in granular formulations. Any relative proportion of fertilizer can be used which is suitable for the crops to which the fertilizing composition is to be applied. The compositions of the invention will commonly comprise from 1% to 25% of the fertilizing composition. These compositions provide fertilizing materials which promote the rapid growth of desired plants, and at the same time control insects.

In addition to DEM and N,N'-dibenzoyl-N'-tert-alkyl-hydrazine compounds, the compositions of this invention may further comprise additional pesticides including: (1) fungicides such as, for example, (a) dithiocarbamates and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithio- carbamate (zineb), zinc propylenebisdithiocarbamate (propineb), sodium methyldithiocarbamate (metham), tetramethylthiuram disulfide (thiram), the complex of zineb and polyethylene thiuram disulfide, 3,5-dimethyl-1,3,5-2H-tetrahydrothiadiazine-2-thione (dazomet); and mixtures of these and mixtures with copper salts; (b) nitrophenol derivatives such as: dinitro-(1-methylheptyl) phenyl crotonate (dinocap), 2-sec-butyl4,6-dinitrophenyl-3,3-dimethylacrylate (binapacryl), and 2-sec-butyl4,6-dinitrophenyl isopropyl carbonate; (c) heterocyclic structures such as: N-trichloromethylthiotetrahydrophthalimide (captan), N-trichloromethylthiophthalimide (folpet), 2-heptadecyl-2-imidazole acetate (glyodine), 2-octylisothiazolone-3,2,4-dichloro-6-(o-chloroanilino)-s-triazine, diethyl phthalimidophosphorothioate, 4-butyl-1,2,4-triazole, 5-amino-1-(bis(dimethylamino)phosphinyl)-3-phenyl-1,2,4-triazole, 5-ethoxy-3-trichloromethyl-1,2,4-thiadiazole, 2,3-dicyano-1,4-dithiaanthraquinone (dithianon), 1,3-dithiolo-(4,5-b)quinoxaline-2-thione (thioquinox), ethyl 1-(butylcarbamoyl)-2-benzimidazole carbamate (benomyl), 2-4'-(thiazolyl) benzimidazole (thiabendazole), 4-(2-chlorophenylhydrazono)-3-methyl-5-isoxazolone, 3-(3,5-dichlorophenyl)-5-ethenyl-5-methyl-2,4-oxazolidinedione (vinolozolin); 3-(3,5-dichlorophenyl)-N-(l-methylethyl)-2,4-dioxo-1-imidazolidinecarboxamide (iprodione); N-(3,5-dichlorophenyl)-1,2-dimethylcyclopropane-1,2-dicarboximide (procymidone); beta-(4-dichlorophenoxy)-alpha-( 1,1-dimethylethyl)-1"H-1,2,4-triazole-1-ethanol (triadimenol); 1-(4-chlorophenoxy)-3,3-dimethyl-1-(1H-1,2,4-triazol-1-yl)-2-butanone (triadimefon); beta-(1, 1'-biphenyl)-4-yloxyl)-alpha-( 1,1-dlimethylethyl)-1H-1,2,4-triazole-1-ethanol (bitertanol); 2,3-dichloro-N-(4-fluorophenyl)maleimide (fluoroimide); 1-(2-(2,4-dichlorophenyl)4propyl-1,3-dioxolan-2-ylmethyl)-1"H-1,2,4-triazole; pyridine-2-thiol-1-oxide, 8-hydroxyquinoline sulfate and metal salts thereof; 2,3-dihydro-5-carboxanilido-6-methyl-1,4-oxathiin-4,4-dioxide, 2,3-dihydro-5-carboxanilido-6-methyl-1,4-oxathiin, alpha(phenyl)-alpha-(2,4-dichlorophenyl)-5-pyrimidinylmethanol (triarimol), cis-N-(1,1,2,2-tetrachloroethyl)thio)-4-cyclohexene-1,2-dicarboximide, 3-(2-(3,5-dimethyl-2-oxycyclohexyl)-2-hydroxy) glutarimide (cycloheximide), dehydroacetic acid, N-(1,1,2,2-tetrachloroethylthio)-3a,4,7,7-tetrahydrophthalimide (captafol), butyl-2-ethylamino4-hydroxy-6-methylpyrimidine (ethirimol), acetate of 4-cyclodecyl-2,6-dimethyl-morpholine (dodemorph), 4-(3-(4-chlorophenyl)-3-(3,4-dimethoxyphenyl)acryloyl)morpholine (dimethomorph), thifluzamide, and 6-methyl-2-oxo-1,3-dithiolo(4,5-b)-quinoxaline (quinomethionate); (d) miscellaneous halogenated fungicides such as: tetrachloro-p-benzoquinone (chloranil), 2-3-dichoro-1,4-napththoquinone (dichlone), 1,4-dichloro-2,5-dimethoxybenzene (chloroneb), 3,56,6-trichloro-o-anisic acid (tricamba), 2,4,5,6-tetrachloroisophthalonitrile (TCPN), 2,6-dichloro-4-nitroaniline (dichloran), 2-chloro-1-nitropropane, polychloronitrobenzenes such as pentachloronitrobenzene (PCNB), and tetrafluorodichloroacetone; (e) fungicidal antibiotics such as: griseofulvin, kasugamycin and streptomycin; (f) copper-based fungicides such as: copper hydroxide, cuprous oxide, basic cupric chloride, basic copper carbonate, copper terphthalate, copper naphthenate and Bordeaux mixture; and (g) miscellaneous fungicides such as: diphenyl, sulfone, dodecylguanidine acetate (dodine), aluminum tris-o-ethyl phosphonate (fosetylal), N-(2,6-dimethylphenyl)-N-(methoxyacetyl)alanine methyl ester(methoxyl) and other alkaline fungicides, phenylmercuric acetate, N-ethylmercuri-1,2,3,6-tetrahydro-3,6-endomethano-3,4,5,6,7,7-hexachlorophthalimide, phenylmercuric monoethanol ammonium lactate, p-dimethylaminobenzene sodium sulfonate, methyl isothiocyanate, 1-thiocyano-2,4-dinitrobenzene, 1-phenylthiosemicarbazide, nickel containing compounds, calcium cyanamide, lime sulfur, 1,2-bis-(3,-methoxycarbony-2-thioureido) benzene (thiophanate-methyl), and 2-cyano-N-(ethylamino)carbonyl)-2-(methoxyimine)acetamide (cymoxanil); as well as acylalanines such as, furalaxyl, cyprofuram, ofurace, benalaxyl, and oxadixyl; fluazinam, flumetover, phenylbenzamide derivatives such as those disclosed in EP 578586 A1, amino acid derivatives such as valine derivatives disclosed in EP 550788 A1, methoxyacrylates such as methyl (E)-2-(2-(6-(2-cyanophenoxy)pyrimidin-4-yloxy)phenyl)-3-methoxyacrylate; benzo(1,2,3)thiadiazole-7-carbothioic acid S-methyl ester: propamocarb; imazalil; carbendazim; myclobutanil; fenbuconazole; tridemorph; pyrazophos; fenarimol; fenpiclonil; pyrimethanil; and tin fungicides; (2) herbicides, such as, (a) carboxylic acid derivatives, including benzoic acids and their salts; phenoxy and phenyl substituted carboxylic acids and their salts; and trichloroacetic acid and its salts; (b) carbamic acid derivatives, including ethyl N,N-di(n-propyl)thiolcarbamate and pronamide; (c) substituted ureas, (d) substituted triazines, (e) diphenyl ether derivatives such as oxyfluorfen and fluoroglycofen, (f) anilides such as propanil, (g) oxyphenoxy herbicides, (h) uracils, (i) nitriles, and () other organic herbicides such as dithiopyr and thiazopyr; and (3) insecticides, including acephate, acethion, acetoxon, aldicarb, aldoxycarb, aldrin, allethrin, allyxycarb, alpha-cypermethrin, amidithion, amitraz, amlure, anethol, azethion, azinphos-ethyl, azinphos-methyl, azocyclotin, bacillus thuringiensis, BCPE, bendiocarb, bensultap, benzoximate, benzyl acetate, benzyl benzoate, BHC, bifenthrin, binapacryl, bomyl, BPMC, bromophos, bromophos-ethyl, bromopropylate, bufencarb, buprofezin, butacarb, butocarboxim, butonate, butoxycarboxim, calcium arsenate, carbaryl, carbofuran, carbophenothion, carbosulfan, cartap, chlordane, chlordecone, chlordimeform, chlorfenethol, chlorfenson, chlorfensulphide, chlorfenvinphos, chlormephos, chlorobenzilate, chloropenozide, chloropropylate, chlorphoxim, chlorpyrifos, chlorpyrifos methyl, chlorthiophos, clofentezine, CPCBS, CPMC, crotoxyphos, crufomate, cryolite, cufraneb, cyanofenphos, cyanophos, cyanthoate, cyfluthrin, cyhexatin, cypermethrin, cyphenothrin, cyromazine, DAEP, DDT, DDVP, deltamethrin, demeton, demetonmethyl, demeton-O-methyl, demeton-S-methyl sulfoxide, demephion-O, demephionS, dialifor, diazinon, dicapthon, dichlofenthion, dicofol, dicrotophos, dieldrin, dienochlor, diflubenzuron, dihydrorotenone, dimefox, dimetan, dimethoate, dimethrin, dinex, dinitrophenol, dinobuton, dinocap, dioxabenzofos, dioxacarb, dioxathion, disparlure, disulfoton, DMCP, DNOC, d-trans allethrin, endosulfan, endothion, endrin, entice, EPBP, EPN, esfenvalerate, ethiofencarb, ethion, ethoatemethyl, ethoprop, etrimfos, fenamiphos, fenazaflor, fenbutatin-oxide, fenitrothion, fenoxycarb, fenpropathrin, fenson, fensulfothion, fenthion, fenvalerate, flubenzimine, flucythrinate, fluenethyl, flufenoxuron, fluvalinate, fonofos, formetanate hydrochloride, formothion, fosmethilan, fosthietan, furathiocarb, furethrin, grandlure, heptachlor, HETP, hexythiazox, hydramethylnon, hydroprene, IPSP, isazophos, isobenzan, isofenphos, isoprocarb, isoprothiolane, isothioate, isoxathi on, jodfenphos, kinoprene, lead arsenate, leptophos, lethane, lindane, lythidathion, malathion, mazidox, mecarbam, mecarphon, menazon, mephosfolan, methamidophos, methidathion, methiocarb, methomyl, methoprene, methoxychlor, methyl parathion, methyl phencapton, mevinphos, mexacarbate, MIPC, mirex, monocrotophos, MTMC, naled, nicotine, nonachlor, omethoate, ovex, oxamyl, oxydeprofs, oxydisulfoton, oxythioquinox, paraoxon, parathion, paris green, permethrin, perthane, phencapton, phenthoate, phorate, phosalone, phosfolan, phosmet, phosnichlor, phosphamidon, phoxim, pirimicarb, pirimiphos-ethyl, pirimiphos-methyl, plifenate, profenofos, promecarb, propargite, propetamphos, propoxur, prothidathion, prothiophos, prothoate, PTMD, pyridaben, pyridaphenthion, quinalphos, resmethrin, ronnell, rotenone, ryania, s-bioallethrin, salithion, schradan, sodium fluosilicate, sophamide, sulfotepp, sulprofos, tefluthrin, temephos, TEPP, terbufos, tetrachlorvinphos, tetradifon, tetramethrin, tetrasul, thallium sulfate, thiocarboxime, thiocyclam hydrogenoxalate, thiometon, tolclofos-methyl, toxaphene, triazamate, triazophos, trichlorfon, trichloronate, triflumuron, trimethacarb, vamidothion, and xylylcarb.

If desired, adjuvants such as surfactants, stabilizers, antifoam agents and antidrift agents and other agrichemically active materials used for their expected utility may be added to the compositions of this invention.

Another embodiment of the present invention is a method for controlling insects comprising applying one or more compositions of this invention to the soil or plant foliage where it is absorbed by the plant, translocated to other plant parts and ultimately ingested by the pest or insects by means of ingestion of one or more of the plant parts. This means of application is referred to as "systemic" application. Alternatively, the embodied compositions may be applied to the soil and contacted therein with the insects and other pests to be controlled. This means of application is referred to as "soil" application. In another alternative, the embodied compositions may be foliarly applied to the plants to be freed from insects and other pests which feed on the foliage.

In this regard then the present invention also contemplates a method of controlling insects comprising contacting insects with an insecticidally effective amount of a composition comprising DEM and one or more N,N'-dibenzoyl-N'-tert-alkyl-hydrazines. The embodied composition can be applied alone or together with a carrier vehicle as noted above. The term "contacting" means applying to at least one of (a) such insects and (b) the corresponding habitat thereof (i.e., the locus to be protected, for example, to a growing crop or to an area where a crop is to be grown) the embodied composition of this invention alone or as a constituent of a larger composition or formulation.

In evaluating the insecticidal activity of the compositions of the present invention, the following test procedures were employed. In these tests, compound 1 is N'-(benzoyl)-N-(4-chlorobenzoyl)- N'-tert-butyl-hydrazine, compound 2 is N-(4-ethylbenzoyl)-N'-(3,5c-dimethylbenzoyl)-N'-tert-butyl-hydrazine, and compound 3 is N'-(3,5-dimethylbenzoyl)-N-(3-methoxy-2-methylbenzoyl)-N'-tert-butyl-hydrazine.

EXAMPLE 1—Evaluation of Compound 1 with and without DEM against the larvae of Colorado potato beetle (*Leptinotarsa decemlineata*)

For each treatment, 2 replicates were performed with a minimum of 90–100 last-instar (L5) newly molted (0–6 hr) larvae. Larvae were ad libitum offered potato foliage that was dipped for 10 seconds in an aqueous solution of DEM, compound 1, or DEM+compound 1. The percent control for each treatment was then determined. Scores were corrected for DEM treated mortality with Abbott's formula (mortality of the DEM treated was 2.5%). These results are summarized in Table 1.

TABLE 1

| Treatment (in ppm by weight) | | |
|---|---|---|
| Compound 1 | DEM | % control |
| 0.0 | 0.5 | 2.5 |
| 0.1 | 0.0 | 18 |
| 0.1 | 0.5 | 73 | ppm = parts per million

These data indicate that the toxicity of compound 1 increased approximately 4-fold since 18% mortality was recorded with compound 1 at 0.1 ppm as compared with 73% mortality with compound 1+DEM (0.1 ppm+0.5 ppm).

EXAMPLE 2—Evaluation of Compound 2 with or without DEM against the larvae of the beet armyworm (*Spodoptera exigua*)

Newly molted (0–6 hr) last (L5) instar larvae were ad libitum offered artificial diet (Smagghe & Degheele, 1996, J. Econ Entomol.) that was uniformly treated with aqueous solutions of DEM, Compound 2, or DEM+Compound 2. 50 μl was applied per well in multi-well Castor tissue culture plates. Per treatment, 2 replicates were performed with n=90–100 larvae. The percent control for each treatment was then determined. Scores were corrected for DEM treated mortality with Abbott's formula (mortality of DEM treated was 0%). These results are summarized in Table 2.

TABLE 2

| Treatment (in ppm by weight) | | |
|---|---|---|
| Compound 2 | DEM | % control |
| 0.0 | 2.5 | 0 |
| 0.5 | 0.0 | 29 |
| 0.5 | 2.5 | 71 | ppm = parts per million

These data indicate that the toxicity of compound 2 at 0.5 ppm could be increased 2.4-fold since 29% of mortality was recorded with compound 2 alone, whereas for the combination compound 2+DEM (0.5 ppmw+2.5 ppm) mortality was increased to 71%.

EXAMPLE 3—Evaluation of Compound 3 with or without DEM against the larvae of the beet armyworm (*Spodoptera exigua*)

Newly molted (0–6 hr) last (L5) instar larvae were ad libitum offered artificial diet (Smagghe & Degheele, 1996, J. Econ Entomol.) that was uniform treated with aqueous solutions of DEM, Compound 3, or DEM+Compound 3. 50 ul was applied per well in multi-well Castor tissue culture plates. Per treatment, 2 replicates were performed with a minimum of n=90–100 last-instar larvae. The percent control for each treatment was then determined. Scores were corrected for DEM treated mortality with Abbott's formula (mortality of DEM treated was 0%). These results are summarized in Table 3.

TABLE 3

| Treatment (in ppm by weight) | | |
|---|---|---|
| Compound 3 | DEM | % control |
| 0.0 | 0.5 | 0 |
| 0.1 | 0.0 | 31 |
| 0.1 | 0.5 | 96 | ppm = parts per million

These data indicate that the toxicity of compound 3 at 0.1 ppm could be increased 3.1-fold since 31% mortality was recorded with compound 3 alone, whereas for the combination compound 3+DEM (0.5 ppm+2.5 ppm) mortality was increased to 96%.

We claim:

1. An insecticidal synergistic composition comprising:

a) a synergistic effective amount of one or more N,N'-dibenzoyl-N'-tert-alkyl-hydrazines of the formula:

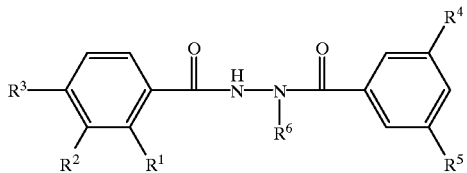

wherein:

i) $R^1$, $R^4$, and $R^5$ are independently hydrogen, $(C_1–C_4)$ alkyl, $(C_1–C_4)$alkoxy, or halo;

ii) $R^2$ and $R_3$ are joined together with the benzoyl ring carbons to which they are attached to form a 5 or 6-membered carbocyclic, dioxolano, dioxano, oxano, or oxolano ring such that when in the form of a 5-membered ring $R^2$ and $R^3$ together is —A—$CH_2$—$A^1$—and when in the form of a 6-membered ring $R^2$ and $R^3$ together is —A—$CH_2CH_2$—$A^1$—, wherein A and $A^1$ are independently —$CH_2$—or —O—; and iii) $R^6$ is a $(C_4–C_{10})$alkyl group containing a tertiary carbon; and b) diethyl maleate;

wherein the ratio of diethylmaleate to N,N'-dibenzoyl-N'-tert-alkyl-hydrazines is from 0.01:1 to 100:1 by weight.

2. The composition of claim 1 further comprising one or more agronomically acceptable carriers.

3. The composition of claim 1 wherein the ratio of diethylmaleate to N,N'-dibenzoyl-N'-tert-alkyl-hydrazines is from 1:1 to 10:1 by weight.

4. A method of controlling insects comprising contacting insects with an insecticidally effective amount of the composition of claim 1.

5. The method of claim 4 wherein the composition further comprises one or more agronomically acceptable carriers.

6. A method for controlling insects comprising applying one or more compositions of claim 1 to soil or plant foliage where it is absorbed by the plant, translocated to other plant parts and ultimately ingested by insects by means of ingestion of one or more plant parts wherein the total amount of N,N'-dibenzoyl-N'-tert-alkyl-hydrazines is from 0.01 Kg. to 10 Kg. of the N,N'-dibenzoyl-N'-tert-alkyl-hydrazine per hectare.

7. A method for controlling insects comprising foliarly applying one or more compositions of claim 1 to the plants to be freed from insects which ingest one or more of the plant parts wherein the total amount of N,N'-dibenzoyl-N'-tert-alkyl-hydrazines is from 0.01 Kg. to 10 Kg. of the N,N'-dibenzoyl-N'-tert-alkyl-hydrazine per hectare.

* * * * *